US009295470B2

(12) United States Patent
Baur et al.

(10) Patent No.: US 9,295,470 B2
(45) Date of Patent: Mar. 29, 2016

(54) RESECTION DEVICE

(75) Inventors: Franziska Baur, Dettingen unter Teck (DE); Chi-Nghia Ho, Stuttgart (DE); Marc O. Schurr, Tuebingen (DE); Gunnar Anhoeck, Reutlingen (DE); Thomas Gottwald, Kochel am See (DE)

(73) Assignee: Ovesco Endoscopy AG, Tuebingen (DE)

( * ) Notice: Subject to any disclaimer, the term of this patent is extended or adjusted under 35 U.S.C. 154(b) by 282 days.

(21) Appl. No.: 12/913,723

(22) Filed: Oct. 27, 2010

(65) Prior Publication Data

US 2011/0208210 A1    Aug. 25, 2011

(30) Foreign Application Priority Data

Oct. 27, 2009  (DE) .......................... 10 2009 050 829

(51) Int. Cl.
*A61B 17/08* (2006.01)
*A61B 17/10* (2006.01)
*A61B 1/00* (2006.01)
*A61B 18/14* (2006.01)
(Continued)

(52) U.S. Cl.
CPC ............. *A61B 17/10* (2013.01); *A61B 1/00087* (2013.01); *A61B 1/00089* (2013.01); *A61B 1/00101* (2013.01); *A61B 17/083* (2013.01); *A61B 18/14* (2013.01); *A61B 17/1227* (2013.01); *A61B 2017/00269* (2013.01); *A61B 2017/00296* (2013.01); *A61B 2017/32006* (2013.01); *A61B 2018/00601* (2013.01); *A61B 2018/00982* (2013.01); *A61B 2018/1407* (2013.01); *A61B 2018/1495* (2013.01)

(58) Field of Classification Search
CPC .. A61B 17/10; A61B 17/1227; A61B 17/083; A61B 1/00101; A61B 1/00089; A61B 2017/0029; A61B 2018/1405; A61B 2018/1407
USPC .................. 606/139, 140, 142, 167, 169, 113
See application file for complete search history.

(56) References Cited

U.S. PATENT DOCUMENTS 5,398,844 A * 3/1995 Zaslavsky et al. ............ 221/208
5,868,760 A   2/1999 McGuckin, Jr.
(Continued)

FOREIGN PATENT DOCUMENTS

DE       103 56 018 A1    7/2004
DE       695 33 454 T2    9/2005
(Continued)

OTHER PUBLICATIONS

European Search Report for EP Application 10188210.8-1269, Feb. 15, 2011.
(Continued)

*Primary Examiner* — Alexander Orkin
(74) *Attorney, Agent, or Firm* — TechLaw LLP

(57) ABSTRACT

A resection device comprising a cup-shaped cap for a shaft-type inserting means is disclosed which is fixed at the distal end of the shaft-type inserting means or is formed at the same and includes an expanding sleeve portion to which a spring-biased tissue clip is attached which can be withdrawn by means of a releasing or withdrawing device over the distal front edge of the cap.
In accordance with the invention, inside the expanding sleeve portion a cutting device is arranged which is held at the inner wall of the expanding sleeve portion at a predetermined axial distance from the distal front edge of the cap.

10 Claims, 8 Drawing Sheets

Figure 1:
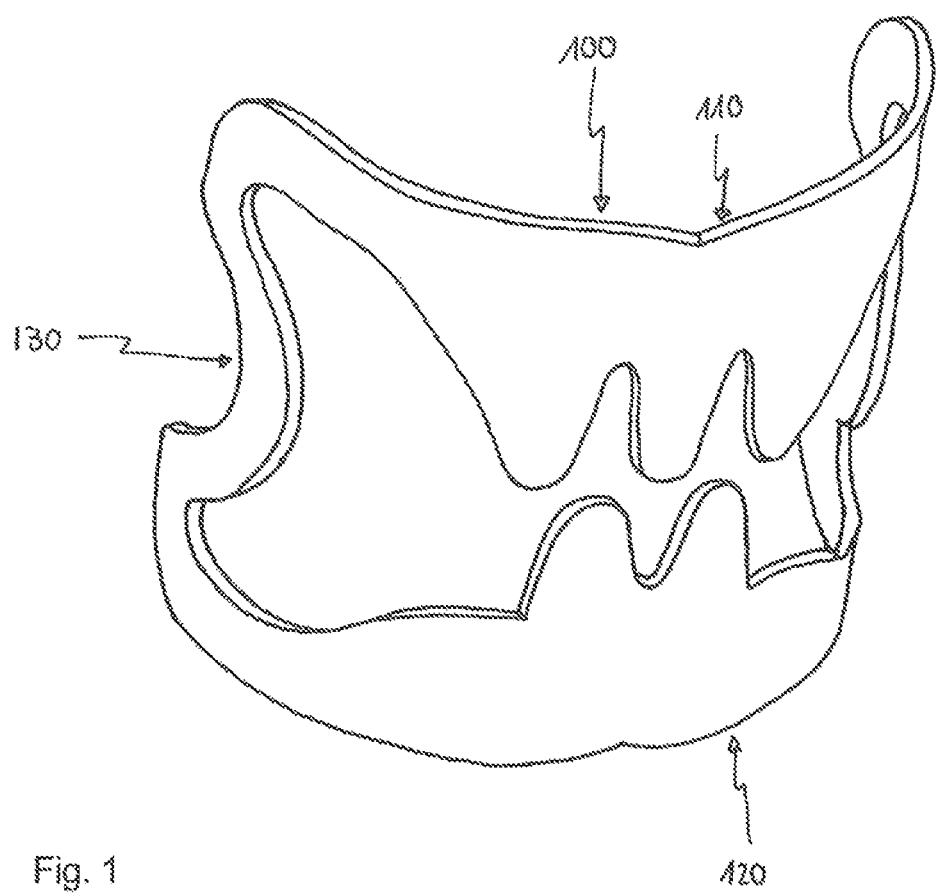

(51) Int. Cl.
    *A61B 17/122* (2006.01)
    *A61B 17/00* (2006.01)
    *A61B 17/32* (2006.01)
    *A61B 18/00* (2006.01)

(56) References Cited

U.S. PATENT DOCUMENTS

| | | | |
|---|---|---|---|
| 6,152,936 A * | 11/2000 | Christy et al. | 606/148 |
| 6,306,081 B1 | 10/2001 | Ishikawa | |
| 6,428,548 B1 * | 8/2002 | Durgin et al. | 606/142 |
| 8,167,893 B2 * | 5/2012 | Motosugi | 606/113 |
| 2002/0035311 A1 * | 3/2002 | Ouchi | 600/175 |
| 2002/0062130 A1 | 5/2002 | Jugenheimer | |
| 2004/0158127 A1 | 8/2004 | Okada | |
| 2004/0210111 A1 | 10/2004 | Okada | |
| 2007/0198000 A1 * | 8/2007 | Miyamoto et al. | 604/523 |
| 2007/0260112 A1 * | 11/2007 | Rahmani | 600/104 |

FOREIGN PATENT DOCUMENTS

| | | |
|---|---|---|
| DE | 20 2008 007 774 U1 | 9/2008 |
| DE | 20 2008 07 774 U1 | 9/2008 |
| WO | WO 99/25255 | 5/1999 |
| WO | WO 2009/150186 A1 | 12/2009 |

OTHER PUBLICATIONS

German Patent Office, German Examination Report for DE 10 2009 050 829.5-35, Jun. 18, 2010 Germany.
Office Action in Japanese Patent Application No. 2010-240213, Dated Jan. 28, 2014.
English Translation of Office Action in Japanese Patent Application No. 2010-240213, Dated Jan. 28, 2014.
Reference JP 2004-230054 cited in the Office Action of Japanese Patent Application No. 2010-240213, Dated Jan. 28, 2014.
English abstract of prior art reference JP 2004-230054 cited in the Office Action of Japanese Patent Application No. 2010-240213, Dated Jan. 28, 2014.

* cited by examiner

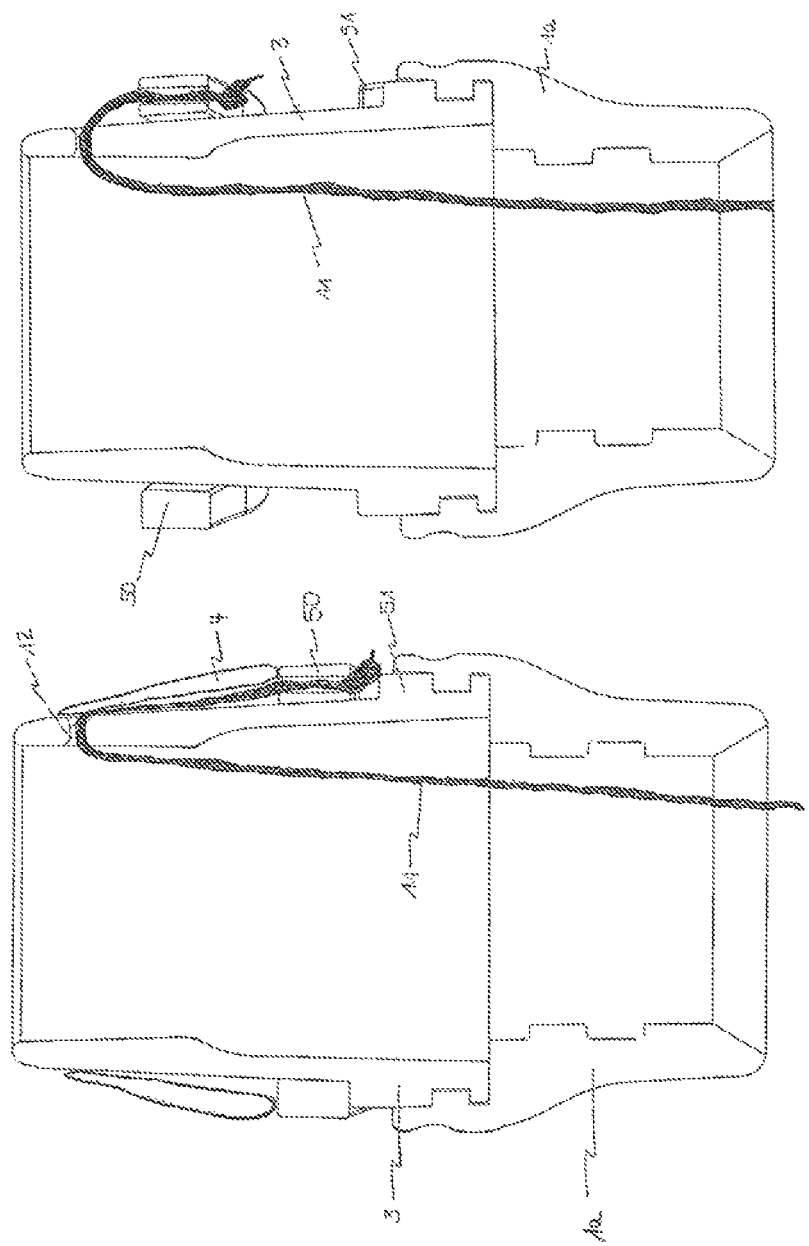

RESECTION DEVICE

The present invention relates to a resection device for minimal-invasive (solid wall) resection of a tissue, for instance a stomach wall or a colon.

Such device makes use of an endoscopic feed means for a tissue clip for closing the tissue cut and a cutting device adapted to be fed via the endoscopic feed means.

From the state of the art, for instance according to U.S. Pat. No. 6,849,078 B2, a tissue clip of this species is generally known as regards its basic construction. For a better comprehension, this clip is hereinafter described in more detail with reference to FIG. 1.

Accordingly, such clip 100 consists of a mouth-like clamping means having two toothed jaws 110, 120 which can be opened and shut via two lateral hinges 130 or via flexible moldings. The hinges 130 or the flexible moldings are preferably formed of spring-elastic straps which when opening the jaws 110, 120 store spring energy which results in snapping the jaws 110, 120 at a predetermined clamping force when the jaws 110, 120 are released, i.e. when the hinges 130 or the flexible moldings are actuated.

In detail, each clip 100 is punched or lasered in one piece out of a spring steel sheet by working a ring having a partially different ring width out of the spring steel sheet. Two diametrically opposed ring portions having a large ring width constitute the two jaws 110, 120, whereas the two ring portions disposed there between having a narrow ring width form the hinges 130 or the flexible (elastic) moldings. The jaws 110, 120 are formed by arching the ring portions having a large ring width in a curved shape over the flat side thereof, whereas the two ring portions having a narrow ring width are twisted about their longitudinal axis by approx. 180° in order to form the hinges. This special shaping of the lasered spring steel sheet creates the shape of a type of shark mouth having two rows of teeth moving toward each other which are formed by laser welding the ring portions having a large ring width.

The functioning of the afore-described medical tissue clip 100 can be described as follows:

In general, an endoscopic implantation of a medical device in total constitutes the most tolerable process for a patient. In this case the medical device must be fixed from the inside of a hollow organ to the latter. For this purpose, a number (at least one) of the afore-described tissue cleats, clips or anchors are inserted into the hollow organ by means of an endoscope or a similar feed means and are positioned at predetermined points at the inner side of the organ. To this end, the respective clip or anchor is brought near the organ tissue and the biasing spring is released for a snapping of the clip or clamping of the anchor. The latter then holds or clamps a tissue fold between its jaws or its hook or needles at a predetermined clamping or expanding force, wherein the teeth, hooks, needles or jags of each jaw cut into the tissue and preferably penetrate the same.

In this way each clip or anchor is anchored at predetermined distances to each other at the inside of the organ.

The endoscope or similar feed means not shown in detail in FIG. 1 usually is equipped with an endoscope head or an endoscope cap which includes, apart from the functions generally required for an endoscope such as lighting, optical system and rinsing means, if necessary, in addition a holding and withdrawing means for the tissue clip. It is referred to the fact in this context that in this entire application also a simple inserting aid without separate lighting and optical system as well as rinsing function can be understood by an endoscope.

The holding and withdrawing means substantially consists of an expanding sleeve as well as a slide operable manually or by remote control which is movable in the longitudinal direction of the endoscope. The expanding sleeve is designed such that the already opened tissue clip can be placed onto the sleeve so that the clip can be prevented from slipping backward while being inserted into the hollow organ. For this purpose, the slide is positioned axially behind the clip and serves so-to-speak as an axial stop for the clip.

As soon as the clip is to be positioned at a particular site, the slide is moved axially forward and in so doing strips off the clip over the expanding sleeve. The clip is actuated, i.e. the biasing mechanism within the clip described before by way of FIG. 1 is released when it is stripped off the expanding sleeve and the two jaws of the tissue clip snap to close while clamping the tissue provided there between.

From another state of the art, for instance according to DE 10/2004 037 830 A1, an endoscope cap equipped with a cutting device is known. The endoscope cap is in the form of a cup-shaped body which is attached to the distal end of an endoscope shaft. The outermost distal edge of the cup is beveled radially inwardly and thus forms an inner contacting surface to which the cutting device is adjacent in the form of a cable loop adapted to be supplied with current. The cable loop is held at the contacting surface via nose-shaped flexible projections at the inside of the cup wall. The cable loop is further connected to the outside via a power supply cable which is movably guided through an endoscope shaft.

In order to remove tissue the cup is put onto the tissue at the distal end of the endoscope and the tissue is sucked into the cup. After that, the wire loop is tightened via the power supply cable, whereby the sucked tissue is constricted. By supplying current to the loop the constricted tissue is severed.

Although it is possible by such device to sever the surface of a colon or stomach wall, for instance, this intervention often is not sufficiently radical in order to remove also diseased tissue which is located more deeply. In this context, it is especially referred to the fact that with such intervention the basic risk of a wall perforation exists which has especially detrimental consequences for a patient.

In view of this state of the art, it is the object of the present invention to develop the known cutting device such that a resection of tissue is possible at a lower risk for the patient.

This object is achieved by a resection device comprising the technical features according to claim 1.

Consequently, the resection device according to the invention includes a cup-shaped cap for a shaft-type inserting means which is adapted to be mounted to the distal end of the shaft-type inserting means or is formed at the same and which has an expanding sleeve portion to which a tissue clip of the afore-mentioned design can be attached that can be withdrawn over the distal front edge of the cap by means of a releasing or detaching device. Inside the expanding sleeve portion a cutting device is disposed which is preferably held at a predetermined axial distance from the distal front edge of the cap via a spacer arranged or formed at the inner wall of the expanding sleeve portion so as to prevent any contact between the tissue clip and the cutting device.

It is possible in this way to suck tissue into the cap in order to then actuate the tissue clip which clamps the tissue directly ahead of the distal front edge of the cap or the expanding sleeve portion. If then the cutting device is activated, the sucked tissue can be severed, the severing line being drawn at a predetermined distance from the tissue clip. This distance is preferably brought about by the spacer and is adjusted such that, on the one hand, the cutting device is safely prevented from contacting the clip and/or, on the other hand, the clip still clamps sufficient tissue in order to safely and tightly close the cut and keep the same closed (without the risk of bursting). As an alternative to this, the cutting device can also be fixed at the inner wall of the expanding sleeve at the predetermined distance from the distal front edge by a detachable support or bonding.

Further preferably a front groove opened on both sides in the circumferential direction of the expanding sleeve portion is formed at the outer circumference of the expanding sleeve for receiving the tissue clip, with a thread, cable or tissue being preferably pulled through the front groove in radial direction as a releasing or withdrawing means. The thread is fixed at one end at the shaft-type inserting means or at the cap and at the other end is movably guided along the shaft-type inserting means so that when pushing the tissue clip into the groove the thread can be entrained by the clip. If subsequently the thread is pulled, it tends to shrink inside the front groove, wherein the tissue clip is pushed out of the groove again by the thread.

As an alternative to this, the thread or the cable or tissue can be fixed at its one end by a wiper ring which is seated to be axially movable on the expanding sleeve behind the attached clip and is displaced forward in the direction of the distal end face of the cap when the thread is pulled. The clip is withdrawn over the distal front edge. In the case of a wiper ring the arrangement of an axial groove can be dispensed with.

Consequently, in this way a constructional division of the holding and withdrawing means according to the invention related to the function is obtained, viz. into the arrangement of the front groove/slit forming an axial stop and into the separate arrangement of a thread simulating a slide or of the slide ring itself operated by the thread. This constructional division of the holding and withdrawing means enables especially the withdrawing means to be formed as a highly flexible thread or cable which requires only little available space and still is adapted to exert sufficiently great displacing forces on the clip especially when using the afore-described block and tackle mechanism.

A preferred configuration of the invention provides to form the cutting device as a cable loop which can be operated and supplied with current via an electric lead guided through the feed means or guided along the feed means.

It is of further advantage to form the expanding sleeve at its distal end portion so as to include an inner shoulder or a circumferential groove which is axially spaced from the distal end face of the sleeve and forms a clamping surface for the cable loop.

In the former event the spacer is manufactured in the form of a ring as a component part separate from the expanding sleeve which is pushed into the sleeve and clamps the loop between itself and the shoulder. In the latter event the spacer can also be formed integrally with the expanding sleeve, the loop being inserted or impressed in the circumferential groove.

Preferably the spacer has an axial length of 2 to 6 mm and especially 2 to 3.5 mm and is substantially flush with the distal front edge of the expanding sleeve.

Further advantageous configurations of the embodiment are the subject matter of the subclaims.

Figure 2:
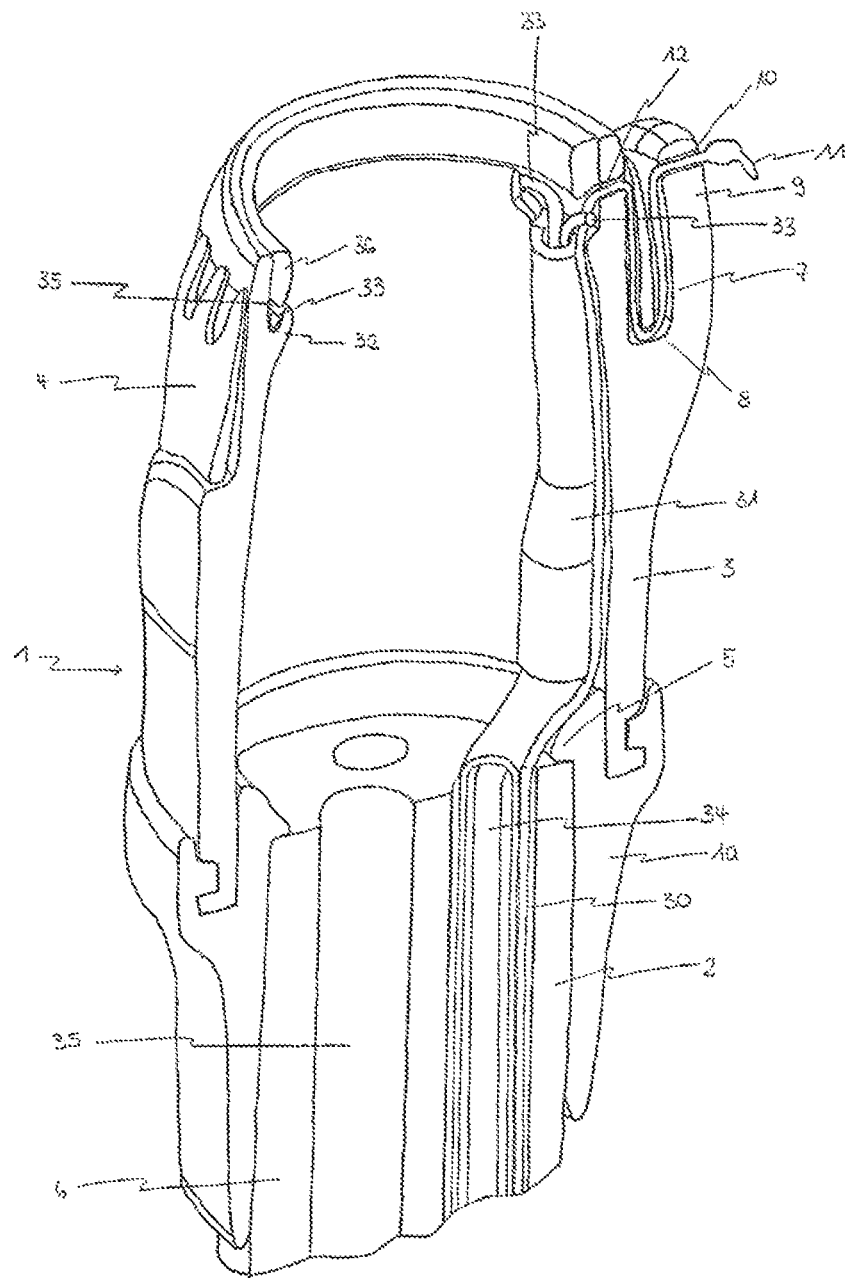
Figure 3:
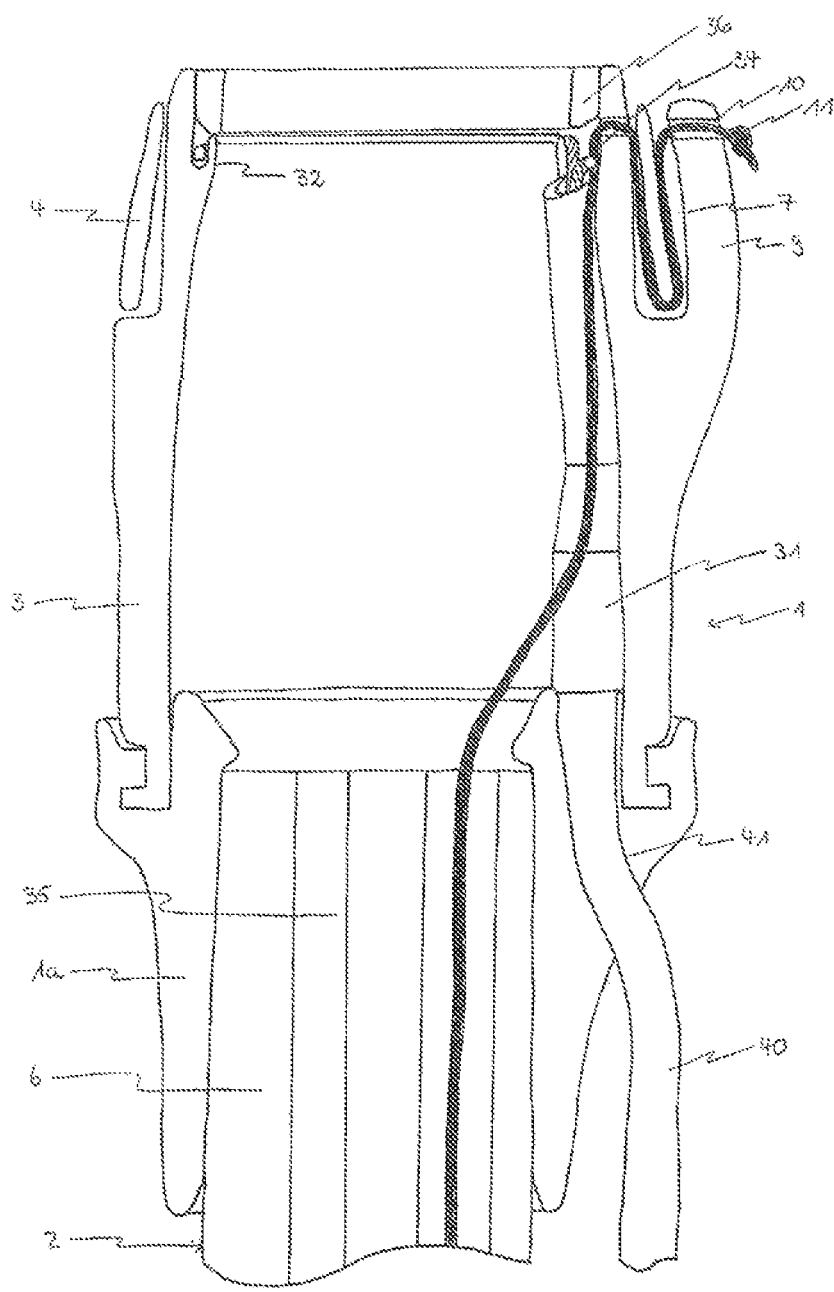
Figure 4:
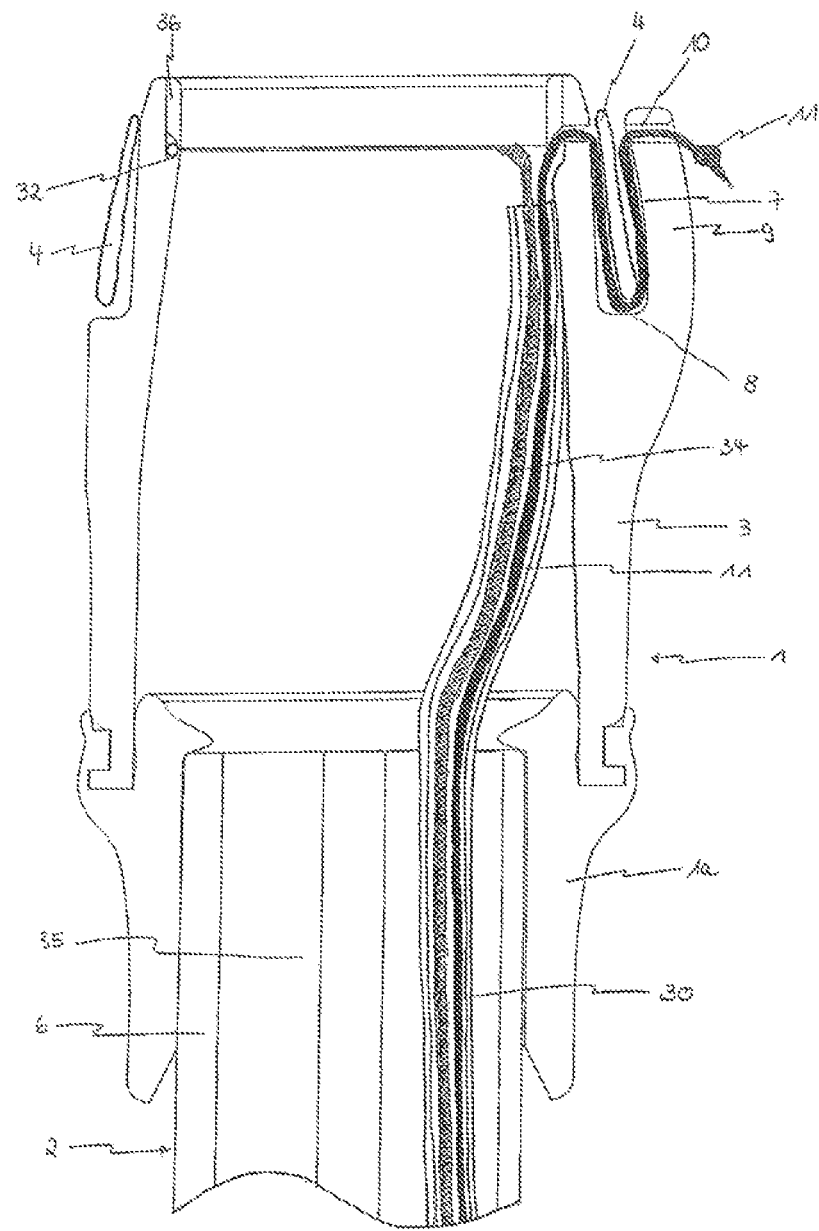
Figure 5:
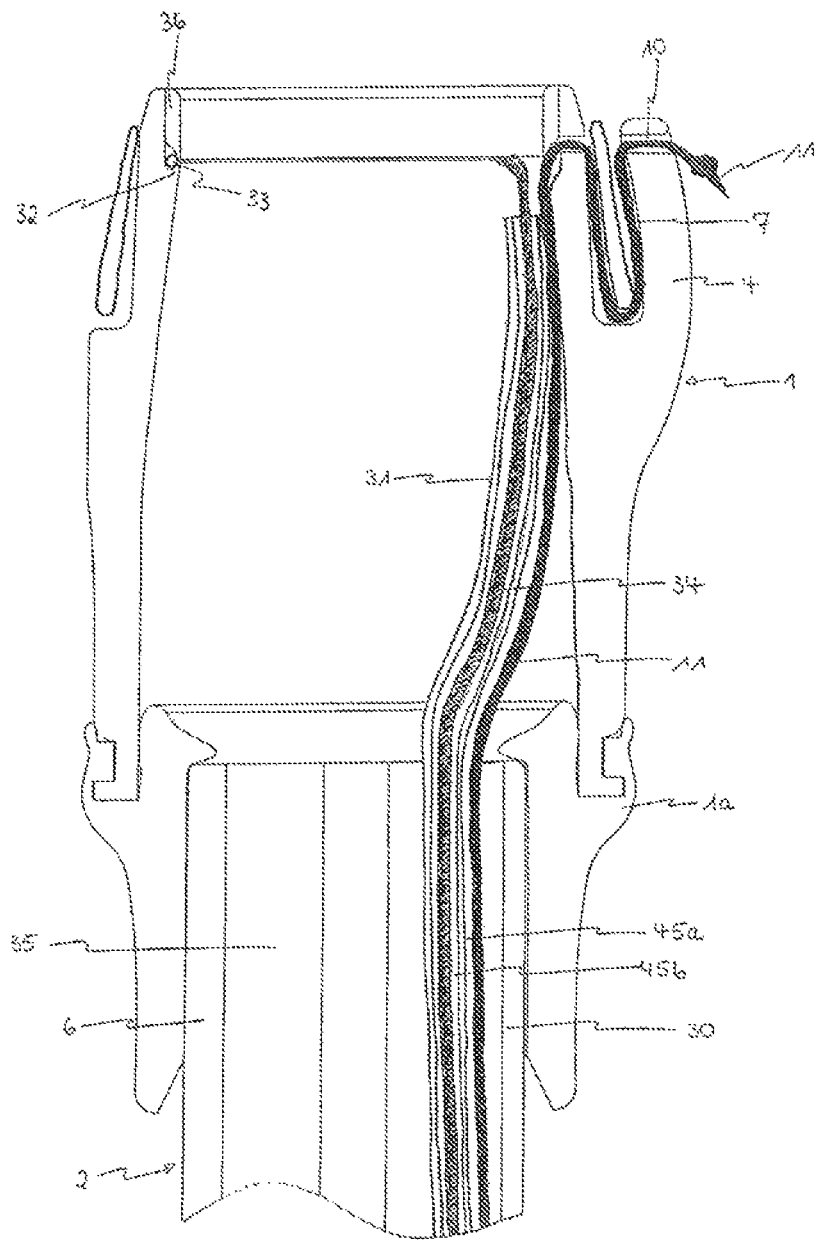
Figure 6:
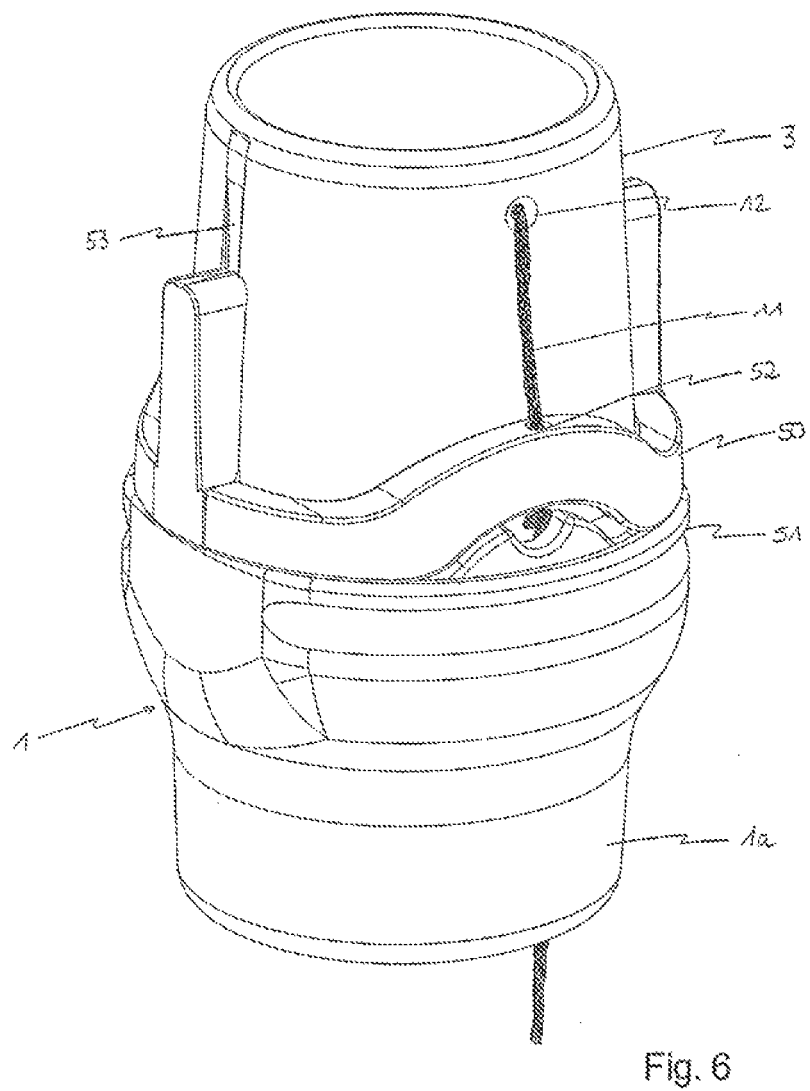
Figure 7:
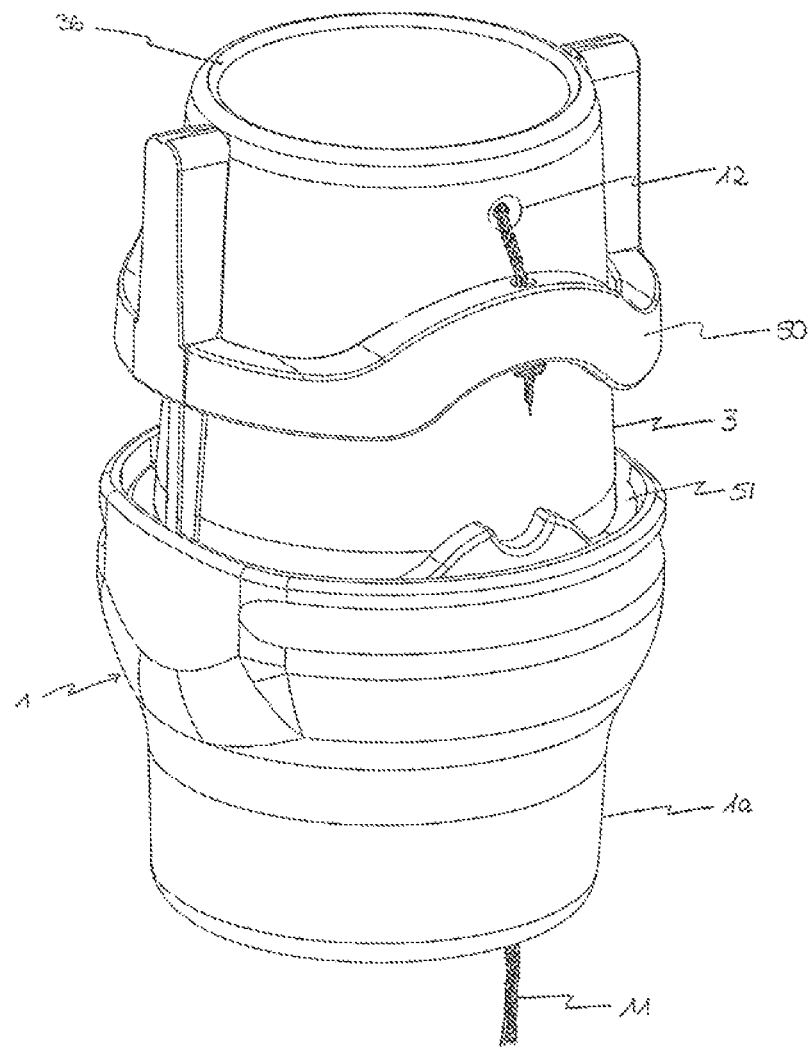

Hereinafter the invention will be explained in detail by way of preferred embodiments with reference to the accompanying drawings, in which FIG. 1 illustrates the exemplary design of a tissue clip in the way as it is known already from the state of the art and as it is equally used in the present invention, FIG. 2 illustrates the longitudinal section of an endoscope cap for a cutting device according to the invention in accordance with a first preferred embodiment of the invention having an attached tissue clip according to FIG. 1 in schematic representation, FIG. 3 illustrates the longitudinal section of an endoscope cap for a cutting device according to the invention in accordance with a second preferred embodiment of the invention having an attached schematically represented tissue clip, FIG. 4 illustrates the longitudinal section of an endoscope cap for a cutting device according to the invention in accordance with a third preferred embodiment of the invention having an attached tissue clip, FIG. 5 shows the longitudinal section of an endoscope cap for a cutting device according to the invention in accordance with a fourth preferred embodiment of the invention having an attached tissue clip, FIG. 6 is the perspective view of an endoscope cap for a cutting device according to the invention in accordance with a fifth preferred embodiment of the invention including an annular discharge means for the tissue clip in the idle state, FIG. 7 is the perspective view of the endoscope cap of FIG. 6 including the annular discharge means for the tissue clip in the operated state and FIG. 8 is a longitudinal view of the endoscope cap of FIG. 5 in the idle state and the operated state.

In FIG. 2 an (endoscope) cap 1 according to a first preferred embodiment of the invention is arranged at the distal end of an endoscope, trocar or similar shaft-type inserting means which is adapted to be inserted into a hollow organ of a human or animal body, for instance the colon or stomach.

The endoscope cap 1 according to the invention has a slip-on portion 1a (preferably a silicone nozzle) which in the mounted state surrounds a distal endoscope head or end portion of the inserting means 2 optionally equipped with endoscope-specific functions, for instance lighting, optical system, rinsing means, mouth of working channel etc. which are individually operable by a handle provided at the proximal end of the endoscope. As an alternative, the inserting aid can also be a simple hollow shaft without any additional functions which has a rigid or flexible design.

The endoscope cap 1 is formed at an axial distance from the slip-on portion 1a at the sheath side into or including an expanding sleeve (expanding sleeve portion) 3 which, in the present embodiment, is positively connected (clipped) to the slip-on portion 1a. It can also be integrally connected to the slip-on portion 1a or glued or welded to the same. A tissue clip 4 as described in the foregoing by way of FIG. 1 and thus likewise belonging to the subject matter of the invention is adapted to be pushed onto the expanding sleeve 3. The expanding sleeve 3 axially projects from the distal end face of the endoscope head 2 and thus forms a cup-shaped sleeve portion radially outwardly rounded at its front edge.

For an exact axial positioning of the endoscope cap 1 the slip-on portion 1a has a radially inner circumferential edge 5 (retainer or stop) which presses against the end face of the endoscope head 2 and thus prevents the endoscope cap 1 from moving along the endoscope in the direction of the proximal end thereof.

In the present first embodiment the endoscope cap 1 is manufactured as a component part separate from the endoscope head 2 which is attached to an already provided housing of the endoscope head 2 (shaft end) optionally including the respective functions and therefore is basically also suited as a retrofit kit of commercial endoscopes or similar shaft-type inserting means. As an alternative, the endoscope cap 1 can also simultaneously constitute the housing for the endoscope head 2 itself and consequently as a component part of the endoscope it can be connected fixedly and tightly to an endoscope shaft 6 which is merely indicated in FIG. 2.

The expanding sleeve 3 according to the invention in each case exhibits a front groove 7 introduced from its distal end face in axial direction in the sheath-side cap or sleeve wall, the groove preferably opening as pitch circle or sickle-shaped (circumferential) slit at the distal end face of the expanding sleeve 3 and the groove bottom thereof forming a stop 8 at an axial rear position, preferably approximately in an axially central portion of the expanding sleeve 3. The radius of the front groove 7 is selected to be larger than the outer radius of the expanding sleeve 3, however, so that when forming the front groove 7 the sleeve wall obtains two slits appropriately spaced in circumferential direction. By forming these front groove sleeves thus the cap shell wall is longitudinally split in this area, whereby a type of tab or tongue 9 defining the radially outer groove wall is formed at the outside of the cap wall.

Another variant of providing a front groove according to the above definition is the additional arrangement of a tab or tongue preferably curved in axial direction, as this is shown especially in FIG. 2, whose root is formed integrally with the cap and which extends axially in the direction of the expanding sleeve while forming the groove at a radial distance from the cap sheath wall. Thus, in this case the shell wall is not split (as described before) but an additional component in the form of the tab is guided over the sheath wall of the cap. This tab can have so narrow dimensions that it remains straight (without radius) in cross-section, i.e. it need not necessarily follow the circumference of the cap. Moreover, the ground plan shape of the tab can be designed largely at will, i.e. it can be thickened and/or widened in the direction of the tab root (transition area between the tab and the cap) in order to obtain higher stiffness. Also the tab root itself can be freely dimensioned and designed according to static aspects so as to obtain maximum stiffness.

Irrespective of the fact according to which manufacturing variant the tab 9 is finally formed, according to the invention it extends from the groove bottom constituting the stop 8 in the direction of the distal end face of the cap 1 or the expanding sleeve 3, wherein the rounded free front edge thereof is axially slightly reset vis-à-vis the distal front edge of the expanding sleeve 3.

As at least indicated in FIG. 2, the front groove 7 does not extend exactly in parallel to the central axis of the cap but is inclined in the direction of the distal end face toward the central axis so that an inserted clip 4 can slip off more easily to the front. Moreover, the groove 7 is not straight but the groove walls thereof, at least the outer groove wall, are slightly curved in axial direction such that the groove 7, at least the tab 9, arches radially outwardly in its axial central portion. In this way, the design according to FIG. 1 geometrically allows or facilitates in this state already the folding behavior of a slipping tissue clip 4.

In an axial front end portion of the tab 9, the same is provided with a radial outer through bore 10 through which a thread 11, cable or tissue is guided from the inside of the groove toward the outside of the cap 1 and is fixed there. Preferably, for this purpose the one thread end is knotted to the outside of the tab so that the thread 11 is prevented from withdrawing through the radial through bore 10. Moreover, at a position substantially radially opposed to the afore-mentioned through bore 10, i.e. in the distal end portion of the axially projecting expanding sleeve 3, the endoscope cap 1 is provided with a radial inner through bore 12 through which the thread 11 is guided from inside the groove into the interior of the expanding sleeve 3.

As one can infer especially from FIG. 2, the inner through bore 12 is provided axially ahead of the distal end side of the endoscope head 2 so that the thread 11 emerging from the inner through bore 12 can be threaded into a function channel opening at the shaft end face or the working channel 30 of the endoscope shaft 6 without having to pass a long free distance. Nevertheless, inside the expanding sleeve 3 a type lining or duct 31 is provided which extends along the sleeve 3 and covers the thread 11 between the inner through bore 12 and the distal end of the endoscope shaft 6.

The inner circumference (inner wall) of the expanding sleeve 3 is bored at its distal end portion over a predetermined axial distance of approx. 2 to 6 mm and preferably 2 to 3.5 mm, thereby an internal shoulder 32 (viewed in feed direction) being formed immediately ahead of the inner through bore 12. Adjacent to said internal shoulder 32 is a cable loop 33 which can be operated and supplied with current via an electric lead 34 guided through the duct 31 and the endoscope shaft 6. Furthermore, in the inner bore 35 a preferably annular spacer 36 is inserted which forces the cable loop 33 against the internal shoulder 32 such that the thread 11 can be pulled out of the inner through bore 12 unhindered.

In this context, it is referred to the fact that, according to the first preferred embodiment of the invention, both the thread 11 and the electric lead 34 are guided in function channels 30 provided for this purpose in the endoscope shaft 6. They can also be laid in a working channel 35, however, through which usually medical instruments are inserted.

As an alternative, it is also possible to lay the thread 11 according to FIG. 3 inside the endoscope shaft 6 and to guide the electric lead 34 via an outer lead channel 40. In this case, according to the second embodiment of the invention, the (endoscope) cap 1 is provided in the area of its slip-on portion is with an axial bore 41 into which the lead channel 40 is inserted and through which the electric lead 34 is guided.

It is also possible, according to the third preferred embodiment of the invention shown in FIG. 4, to freely guide the electric lead 34 as well as the thread 11 in the same function channel 30 inside the endoscope shaft 6. An alternative to this according to FIG. 5 provides to guide the electric lead 34 and the thread 11 in separate tubes 45*a*, 45*b* which, in turn, are laid inside a function channel 30 of the endoscope shaft 6 and thus separate the thread 11 from the electric lead 34.

In accordance with FIG. 2, the spacer 36 is manufactured as a separate component inserted in the expanding sleeve 3. As an alternative to this, also the expanding sleeve 36 can be formed to have, at its inside, in the area of the shown internal shoulder 32 a circumferential groove into which the cable loop 33 can be impressed. Also, the cable loop 33 could be detachably glued or attached to the inner wall of the expanding sleeve 3. Finally, it is also possible to chamfer the inner circumferential groove in axial direction so as to provide a receiving space for the cable loop 33. Preferably the spacer can be manufactured of a flexible or elastic material such as silicone which facilitates removing the cable loop 33.

In all above-mentioned variants it is crucial that the cable loop 33 is held at a predetermined axial distance of preferably 2 to 6 mm from the distal end face of the cap 1 until it is released by tension via the electric lead 34, i.e. it is withdrawn from the inner wall of the expanding sleeve 3.

The operation of the endoscope cap 1 according to the invention including the holding and withdrawing function for the tissue clip 4 as well as of the cutting device is hereinafter described in detail.

In order to move a tissue clip 4, for instance according to FIG. 1, to its predetermined position first of all it has to be pulled onto the expanding sleeve 3 of the endoscope cap 1. For this purpose, the lower and upper jaws of the tissue clip 4 are manually opened so that the clip 4 can be attached to the rounded front edge of the expanding sleeve 3 and can be pushed over the same. The rear edge of the tissue clip 4 penetrates the front groove 7 of the endoscope cap 1 and pulls the thread 11 out of the function or working channel 30 of the endoscope shaft 6.

Finally the displacing movement of the clip 4 comes to a standstill when it contacts the groove bottom 8, wherein the clip 4 and the entrained thread 11 adopt the position shown in FIG. 2. That is to say, in this position the clip 4 is completely pulled onto the endoscope cap 1 and in this way can be introduced via the endoscope 2 into a hollow organ. The thread 11 encompasses the rear edge of the clip 4 and thus is given a U-shape viewed in the longitudinal direction of the thread.

As soon as the resection device according to the invention has reached a diseased site within a hollow organ, the expanding sleeve 3 is pressed against the organ wall and the wall is pulled into the expanding sleeve 3 by negative pressure inside the expanding sleeve 3 and/or by means of forceps or a similar gripping instrument inserted via the endoscope shaft 6 (the working channel 35 thereof). If the clip 4 now is to be stripped off, the thread 11 which is guided through the shaft channel 30 to the proximal end of the endoscope 2 is pulled, wherein the thread portion crossing the front groove 7 in radial direction shrinks. Since the thread 11 is fixed in the outer through bore 10, it exerts a force in axial direction on the clip 4 with an appropriate ratio according to the block and tackle principle, thereby the clip 4 being displaced in the direction of the distal end of the endoscope cap 1. The outer rounding of the front expanding sleeve edge and the soft, viz, arched shaping of the front groove 7 (especially the tab 9) facilitate sliding of the clip 4 over the front edge of the expanding sleeve 3 and further reduce the maximum displacing force to be applied via the thread 11. As soon as the rear edge of the clip 4 has left the front groove 7 and therefore can no longer be held by the tab 9, the biasing force stored in the clip 4 causes the clip 4 to come off the expanding sleeve 3, thereby the organ wall being pinched off in the area directly ahead of the expanding sleeve 3.

Now the cutting device can be operated. For this purpose, the electric lead 34 is pulled, whereby the cable loop 33 detaches from the inner wall of the expanding sleeve 3 and constricts the pulled-in organ wall approx. 2 to 6 mm ahead of the tissue clip 4. By supplying high-frequency current to the loop 33 the pulled-in wall is shorn off. Thus the organ wall resection is completed and the endoscope 2 can be removed from the hollow organ along with the shorn wall piece, the clip 4 closing the wound.

In this context it is further referred to the fact that the cutting device defined as cable loop 33 represents only one variant and can be replaced with a different type of cutting device, for instance a blade or scissors dosing like a rosette.

FIGS. 6 to 8 show another embodiment of the invention, wherein hereinafter merely the features different from the above embodiments shall be discussed.

As one can infer from FIG. 6, the strip-off device of the fifth preferred embodiment of the invention consists of a strip ring 50 which is pulled onto the expanding sleeve 3 and is adjacent to an outer shoulder 51 in the central area of the endoscope cap 1. As an alternative to this, the strip ring 50 can also be axially adjacent to the groove bottom of a front groove in accordance with any one of the preceding embodiments.

In the fifth embodiment no tab or front groove is provided. Instead, the thread 11 guided through the inner through bore 12 is fastened directly at the strip ring 50 as in the latter a through bore 52 is introduced through which the thread 11 is guided and fixed in the same. Moreover, at the outer circumference of the expanding sleeve 3 an axial bar 53 or an axial groove is formed so as to engage in an axial internal groove of the strip ring 50 or an axial inner bar and to form an axial guide for the strip ring 50. For the rest, as regards its shape the strip ring 50 is adapted to the tissue clip (not shown in FIG. 6) so that the latter can be applied substantially custom-fit to the ring 50.

The functioning of the resection device of the fifth embodiment of the invention can be described as follows by way of the FIGS. 6 to 8.

As soon as a diseased organ wall is pulled into the expanding sleeve 3 by negative pressure and/or forceps (gripping instrument), the tissue clip is withdrawn. To this end, the thread 11 has to be pulled along the endoscope shaft, whereby the strip ring 50 moves forward in the direction of the distal front edge of the expanding sleeve 3. Accordingly, also the clip is moved forward, until it comes off by the spring bias thereof over the distal front edge of the expanding sleeve 3 and pinches the organ tissue between its jaws. After that the pulled-in tissue can be shorn off by means of the cutting device inside the expanding sleeve 3.

The invention claimed is:

1. A resection device comprising:
a cup-shaped cap for a shaft-type inserting means which cap is mounted to or formed with the distal end of the shaft-type inserting means and which cap includes an expanding sleeve portion providing an outer circumferential surface at which a mouth-shaped elastic tissue clip is slipped on, such that the tissue clip is removable from the expanding sleeve portion by axially shifting the tissue clip,
wherein the tissue clip is displaceable toward the distal front edge of the cap by an axial force-applying means, and
wherein the tissue clip is removable via displacement toward the distal front edge of the cap, and
wherein an inner wall of the expanding sleeve portion is bored at its distal end portion over a predetermined axial distance of approximately 2 to 6 mm, thereby an internal shoulder being formed, and
wherein at the inner wall of the expanding sleeve portion, a spacer is arranged in the form of a ring and a circumferential groove is shaped between the spacer and the inner shoulder, and
wherein inside the expanding sleeve portion, a cutting device is arranged which is held at the inner wall of the expanding sleeve portion at a predetermined axial distance from the distal front edge of the cap, and
wherein the cutting device is a cable loop inserted into the circumferential groove formed at the inner wall of the expanding sleeve portion at the predetermined axial distance from the distal front edge of the cap, and further wherein two free portions of the cable loop are fed into a single function channel extending along the shaft-type inserting means thereby forming a width-adjustable closed loop when being retracted within the single function channel.

2. The resection device according to claim 1, wherein at the inner wall of the spacer portion the circumferential groove is bored at the predetermined axial distance from the distal front edge of the cap, thereby the spacer being formed integrally with the cap.

3. The resection device according to claim 1, wherein the cutting device is operated and supplied with current via an electric lead.

4. The resection device according to claim 3, wherein the axial force-applying means is a thread, cable or tissue which is guided through the interior of the cap and is guided either around the distal front edge or through a radial through bore directly ahead of the distal front edge in the expanding sleeve portion to the outside so as to pull the tissue clip in the direction of the distal front edge.

5. The resection device according to claim 4, wherein a front groove opened on both sides in the circumferential direction of the expanding sleeve portion is formed at the outer circumference of the expanding sleeve portion for axially receiving the tissue clip through which front groove the thread, cable or tissue is pulled in radial direction and is fixed at a free end of the cap.

6. The resection device according to claim 4, wherein the thread, cable or tissue is fixed at its one free end to a strip ring which is seated to be axially movable on the expanding sleeve portion behind the tissue clip in its slipped-on position and, when pulling the thread, is movable forward in the direction of the distal end face of the cap while pressing away the tissue clip ahead.

7. The resection device according to claim 4, wherein the inserting means is an endoscope having an endoscope shaft in which a working channel for feeding a medical instrument is formed.

8. The resection device according to claim 7, wherein the electric lead and the thread, cable or tissue are guided inside the endoscope shaft in the working channel or a function channel parallel thereto.

9. The resection device according to claim 7, wherein the thread, cable or tissue is guided inside the endoscope shaft and the electric lead is guided outside the endoscope shaft in an external tube.

10. The resection device according to claim 1, wherein the predetermined axial distance is 2 to 3.5 mm.

* * * * *